(12) United States Patent
Jacoby

(10) Patent No.: US 6,686,498 B2
(45) Date of Patent: Feb. 3, 2004

(54) PROCESS FOR THE PREPARATION OF MICHAEL-ADDUCTS

(75) Inventor: Denis Jacoby, Nyon (CH)

(73) Assignee: Firmenich SA, Geneva (CH)

(*) Notice: Subject to any disclaimer, the term of this patent is extended or adjusted under 35 U.S.C. 154(b) by 0 days.

(21) Appl. No.: 10/077,551

(22) Filed: Feb. 14, 2002

(65) Prior Publication Data

US 2002/0128504 A1 Sep. 12, 2002

Related U.S. Application Data

(63) Continuation of application No. PCT/IB01/00318, filed on Mar. 7, 2001.

(51) Int. Cl.$^7$ .............................................. C07C 69/66
(52) U.S. Cl. ....................................................... 560/174
(58) Field of Search ........................................ 560/174

(56) References Cited

U.S. PATENT DOCUMENTS 5,017,649 A * 5/1991 Clemens ...................... 525/59
5,847,186 A   12/1998 Shibasaki et al.
6,090,969 A    7/2000 Shibasaki et al.

FOREIGN PATENT DOCUMENTS

EP  0088423    9/1983
EP  0826652    3/1998
EP  0826652  * 4/1998

OTHER PUBLICATIONS

Kocovsky et al, Collection Czechoslovack Chem. Commun. vol. 53, 1988 pp. 2667.*
Garcia–Raso,et al, Synthesis 1982, vol. 12 pp. 1037–1041.*
Baruah et al, Indian Journal of Chemistry, vol. 37 B 1998, pp. 425–426.*
Kotsuki et al, Tetrahedron Letters, vol. 38, No. 43, pp. 7583–7586.*
J.D. Surmatis et al, "A Study on the Condensation of Mesityl Oxide with Acetoacetic Ester" Technical Dept, Hoffman–La Roche, vol. 35, No. 4, pp. 1053–1056; (1970).
Pavel Koĉovsky et al. "Transition–Metal catalysts in Michael Addition of β–Dicarbonyls:Tuning Of The Reaction Conditions"; Tetrahedron Letters, vol. 27, No. 41, pp. 5015–5018 (1986).
Pavel Koĉovsky et al. "Transition–Metal catalysts in Michael Addition of β–Dicarbonyls:Tuning Of The Reaction Conditions"; Collections Czechoslovak Chem. Commun., vol. 53, pp. 2667–2674 (1986).
William G. Dauben et al. "Organic Reactions At High Pressure: Michael Addition of Activated Acyclic Donors with β, β–Distributed Enone Acceptors", Tetrahedron Letters, vol. 24, No. 36, pp. 3841–3844 (1993).

Alfonso Fernandez–Mateos, "Synthesis of Active Antifeedant CDE Fragments of 11–Ketoepoxyazadiradione Based on an Electrocyclization Reaction Catalyzed by Perchloric Acid,"Journal of Org. Chem., vol. 63, pp. 9440–9447 (1998).
A.M. El–Gendy, "Some reactions of diethy 2,3,4,6,7,8,9, 10–octahydro–2, 6–dioxo–4, 8–diphenyl–4a, 8a–anthracenedicarboxyklate with nitrogen and carbon nucleophiles" Asian J. Chem, vol. 2 (2) pp. 168–169 (1990).
Yuan L. Chow etal., "The photocycloaddition of dibenzoylmethanatoboron difluoride (DBMBF$_2$) with conjugated enones and en–esters" Can. J. Chem 71, Vol 71, pp. 846–854 (1993).
Abstract (XP–002195727) Soriente et al, K10 Montmorillonite catalysis, Royal Society of Chemistry,pp 157–162 (1999).
Abstract (XP–002195726) pp. 1–2.
Soriente et al. Solvent Free Reaction Under Microwave Irradiation: A New Procedure For EU+3–Cataly6zed Michael Addition of 1,3–Dicarbonyl Compounds, Elsevier Science Ltd., Tetrahedron Letters, vol. 38, No. 2, pp. 289–290 (1997).
H. Kotsuki et al., Yb(Otf)$_3$–Catalyzed Michael Addition Reactions of β–Ketoesters on Silica Gel Supports and at High Pressure$^{1"}$ Dept. of Chemistry, Tetrahedron Letters, vol. 38, No. 43, pp. 7583–7586 (1997).

* cited by examiner

Primary Examiner—Alan L. Rotman
Assistant Examiner—Hector M Reyes
(74) Attorney, Agent, or Firm—Winston & Strawn LLP

(57) ABSTRACT

The present invention relates to the field of organic synthesis and more specifically to a process for the preparation of Michael-adducts, as defined below, by reacting a β,β- or a α,β-disubstituted, or a α,β,β-trisubstituted, α,β-unsaturated ketone (I) with a β-ketoester or a β-diketone (II) in presence of a suitable catalyst of formula M(X)$_n$, according to scheme 1:

Scheme 1: The process of the invention

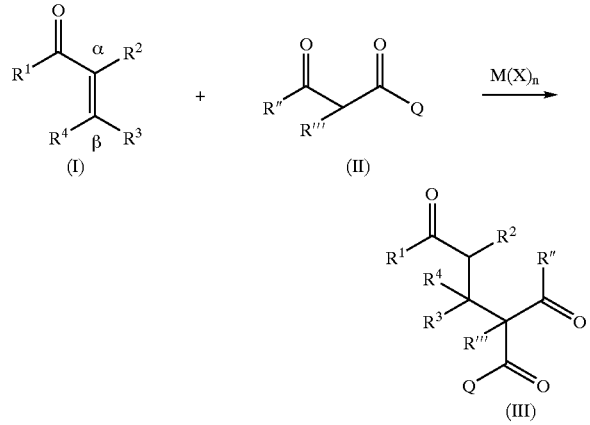

15 Claims, No Drawings

PROCESS FOR THE PREPARATION OF MICHAEL-ADDUCTS

This is a continuation of prior application No. PCT/IB01/00318 filed Mar. 7, 2001.

TECHNICAL FIELD

The present invention relates to the field of organic synthesis and more specifically to a process for the preparation of Michael-adducts, as defined below, by reacting a β,β- or a α,β-disubstituted, or a α,β,β-trisubstituted, α,β-unsaturated ketone (I) with a β-ketoester or a β-diketone (II) in presence of a suitable catalyst of formula $M(X)_n$, according to scheme 1:

Scheme 1: The process of the invention

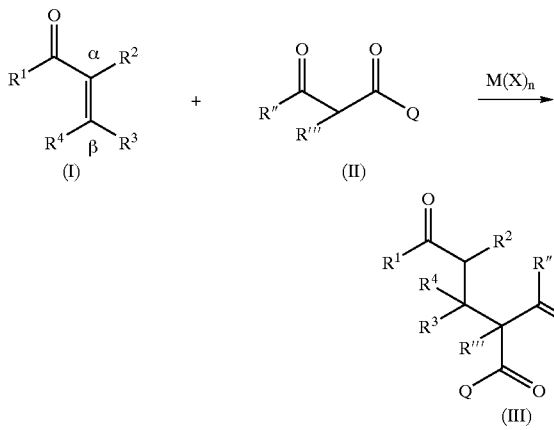

PRIOR ART

To the best of our knowledge, no reaction according to scheme 1 involving a α,β-disubstituted, or a α,β,β-trisubstituted, α,β-unsaturated ketone with a β-ketoester or a β-diketone has been reported in the prior art.

Various processes involving addition reactions between β,β-disubstituted α,β-unsaturated ketones and β-ketoester or a β-diketone in the presence of a base have been reported before. However, they all provide a product which is the result of a so-called Robinson annulation, e.g. as described in J. D. Surmatis et al., *J Org. Chem.*, (1970), 1053.

The coupling of a β,β-disubstituted enone with an alkyl β-ketoester in the presence of 5% of a metal/acac complex (acac being 2,4-pentanedione) and 5% of a Lewis or a Brönsted acid (P. Kocovsky et al., *Tetrahedron Lett.*, (1986), 5015 or P. Kocovsky et al., *Coll. Czech. Chem. Commun.*, (1988), 2667) has also been tried, but the β,β-disubstituted enones used by these authors proved to be inert under a variety of conditions.

Similarly, the direct coupling of the same type of compounds under high pressures (W. G. Dauben et al, *Tetrahedron Lett.*, (1983), 3841), has shown that a Michael-adduct can only be obtained if a highly reactive β,β-disubstituted enone, such as the 3,4,5,6-tetrahydro-1(2H)-pentalenone, is used. Another example of the synthesis of a Michael-adduct, by using highly activated β,β-disubstituted α,β-unsaturated ketones, possessing a C=C double bond moiety as part of a bycyclic ring, is described in A. M. El-Gendy et al. *Asian. J. Chem.*; (1990), 2, 168.

U.S. Pat. Nos. 4,939,143 and 4,900,754 report the synthesis of 3,3-dimethyl-2-(4-fluoro-3-methylbenzoyl)-5-oxohexanoate. In said synthesis a β,β-disubstituted enone is reacted with a β-ketoester in presence of a stoechiometric amount of $BF_3·OEt_2$ at 0° C. However, this method has the major drawback to need a stoechiometric amount of an expensive, strong and reactive Lewis acid. Furthermore, said method, which has been reported only for the specific reaction described in the US patents, cannot be considered as a general method because if a β-diketone is used instead of β-ketoester then the reaction leads directly to the Robinson annulation product, as described in A. Fernandez-Mateos et al. *J. Org. Chem.*; (1998), 63, 9440.

Y. L. Chow; *Can. J. Chem.*, (1993), 71, 846 teaches about the photochemical reaction between a β,β-disubstituted enone and a $B(acac)F_2$ complex. Nevertheless, said reaction leads to the formation of several by-products and, additionally, needs a steochiometric amount of $BF_3$.

Although compounds of formula (III) are interesting intermediates in a number of synthesis, and can also be precursors of β,β-disubstituted-δ-diketonic or α,β-disubstituted-δ-diketonic compounds, to the best of our knowledge, none of the methods reported for their preparation is of general or of simple application.

DESCRIPTION OF THE INVENTION

In order to overcome the difficulties aforementioned, the present invention relates to a simple and general process, aimed at the synthesis of the compounds of formula (III) in a single step.

In this process, the preparation of a compound of formula (III):

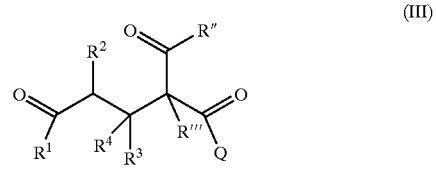

wherein

Q represents a R' group, a OR' group, or a $NH_2$, NHR' or $NR'_2$ group;

$R^1$, R' and R" represent, independently from each other, an aromatic ring possibly substituted, or a linear or branched $C_1$–$C_8$ alkyl or alkenyl group, possibly substituted;

R''' represents a hydrogen atom or a linear or branched $C_1$–$C_4$ alkyl or alkenyl group;

$R^2$, $R^3$, $R^4$, represent, independently from each other, a hydrogen atom or an aromatic ring possibly substituted, or a linear, branched or cyclic $C_1$–$C_8$ alkyl or alkenyl group, possibly substituted, provided that at least two of said $R^2$, $R^3$ and $R^4$ groups do not represent simultaneously an hydrogen atom; or two of the groups $R^1$ to $R^4$ are bonded together to form a ring having 5 to 15 carbon atoms, said ring being possibly substituted;

characterized in that a β,β- or a α,β-disubstituted, or a α,β,β-trisubstituted, α,β-unsaturated ketone (I)

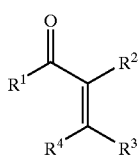
(I)

wherein $R^1$, $R^2$, $R^3$ and $R^4$ have the same meaning as in formula (III),
is reacted with a β-ketoester or a β-diketone (II)

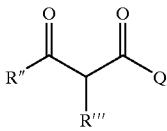
(II)

wherein Y, R" and R'" have the same meaning as in formula (III),
in the presence of a catalyst of formula $M(X)_n$, M representing a metal or a group containing a metal, n representing an integer from 1 to 4 and X representing a weakly coordinating or non-coordinating mono-anion.

As non-limiting examples, groups which are possible substituents of $R^1$, $R^2$, $R^3$, $R^4$, R', R" and of the ring, which two of said R' to $R^4$ may form together, are $C_1$–$C_7$ alkyl, alkenyl or alkoxy groups, $C_5$–$C_7$ cycloalkyl or cycloalkenyl groups, or aromatic rings possibly substituted by a $C_1$–$C_8$ alkyl or alkoxy group or a halide atom.

Preferably,

Q represents a R' or a OR' group;

R', R' and R" represent, independently from each other, a linear $C_1$–$C_5$ alkyl or alkenyl group, possibly substituted;

R'" represents a hydrogen atom or a linear or branched $C_1$–$C_3$ alkyl group;

$R^2$, $R^3$ and $R^4$ represent a hydrogen atom or a linear $C_1$–$C_5$ alkyl or alkenyl group, possibly substituted, provided that at least two of said $R^2$, $R^3$ and $R^4$ groups do not represent simultaneously an hydrogen atom; or two of the groups $R^1$ to $R^4$ are bonded together to form a ring having 5 to 8 carbon atoms, said ring being possibly substituted.

As non-limiting examples, groups which are possible substituents of $R^1$, $R^2$, $R^3$, $R^4$, R', R" and of the ring, which two of said $R^1$ to $R^4$ may form together, are $C_1$–$C_4$ alkyl, alkenyl or alkoxy groups, $C_5$–$C_6$ cycloalkyl or cycloalkenyl groups or aromatic groups possibly substituted by a $C_1$–$C_6$ linear or branched alkyl or alkoxy group or a halide atom.

More preferably, the compound of formula (I) is 4-methyl-3-penten-2-one or 3-methyl-3-penten-2-one, and the compound of formula (JI) is 2,4-pentanedione or a $C_1$–$C_4$ alkyl ester of the 3-oxo-butanoate.

Preferred catalysts of formula $M(X)_n$ are those wherein M is selected from the group consisting of the 3d transition metals, the lanthanides, the trimethylsilane group ($Me_3Si$), the vanadyl group ($VO^{3+}$), the alkaline metals, Sc, Y, Sn, Pb, Al and Bi;

n is an integer from 1 to 3; and

X is selected from the group consisting of $CF_3SO_3^-$, $RSO_3^-$, $SbF_6^-$, $PF_6^-$, $ClO_4^-$, $[BF_3(RCOCRCOR)]^-$, $[BF_3(RCOCRCO_2R)]^-$, $[BF_3(RCOO)]^-$, $[BF_3(RO)]^-$, $BZ_4^-$, Z being a fluoride atom or an alkyl or aryl group possibly substituted, and R representing an $C_1$–$C_{10}$ aromatic, alkylaromatic or alkyl group, possibly substituted.

Groups which are possible substituents of Z and R are, for example, halides atomts, $C_1$ to $C_6$ alkyl or alkoxy groups or non-coordinatng nitrogen containing groups.

More preferably M is selected from the group consisting of Cu, Zn, Y and Yb;

n is an integer from 1 to 3; and

X is selected from the group consisting of $CF_3SO_3^-$, $C_6H_5SO_3^-$, $CH_3C_6H_4SO_3^-$, $CH_3SO_3^-$, $SbF_6^-$, $PF_6^-$, $ClO_4^-$, $[BF_3(acac)]^-$ (acac representing $CH_3COCHCOCH_3^-$), $[BF_3(CH_3COO)]^-$, $BF_4^-$ and $BPh_4^-$.

In general, the catalyst may be added to the reaction media as a pure and isolated chemical or it can be prepared in situ, by several methods, in the reaction medium, without isolation or purification, just before its use.

One of the possible procedures to advantageously prepare in situ a catalyst according to the invention consists in reacting an appropriate anhydrous metal salt of formula $M(acac)_n$ or $M(RCOO)_n$, R being defined as herein above and n being an integer from 2 to 3, with n equivalents, in respect to the metal, of $BF_3 \cdot OEt_2$ in a solvent, e.g. an ester. The mixture thus obtained is ready to be used in the process of the invention. Alternatively, it is possible to use a hydrate form of a catalyst of the invention, which is generally commercially available, and to proceed to a dehydration, using any of the conventional methods of the art, prior the use of said catalyst in the process.

The catalyst can be added to the reaction medium in a large range of concentration. As non-limiting examples, one can cite as catalyst concentration values ranging from 0.001 to 0.1 molar equivalents, relative to the α,β-unsaturated ketone (I). Preferably, the catalyst concentration will be comprised between 0.005 and 0.05 molar equivalents. It goes without saying that the optimum concentration of catalyst will depend on the nature of the latter and on the desired time of reaction.

The process of the invention can be carried out in presence or absence of solvent, but in any case it is advantageously performed in anhydrous conditions, wherein by anhydrous is intended a content in water below 1% by weight, preferably below 0.5%. When a solvent is required, it is possible to use a pure solvent or a mixture of solvents. Said solvent is chemically compatible with the reaction and does not deactivate the catalyst, e.g. a weakly or non-coordinating solvent. Preferred solvents for the process of the invention are selected from the group consisting of ethers, carboxylic acids, esters, ketones, aromatic solvent, linear or branched or cyclic hydrocarbons, chlorinated solvents and mixture thereof. More preferably, the solvent is selected from the group consisting of $C_4$–$C_6$ ethers, $C_2$–$C_8$ esters, $C_3$–$C_6$ ketones, acetic acid, methylene chloride and mixture thereof.

The temperature at which the process of the invention can be carried out is comprised between –20° C. and 100° C., preferably between 0° C. and 50° C. Of course a person skilled in the art is also able to select the preferred temperature as a function of the melting and boiling point of the starting and final products and/or an eventual solvent.

The process of the invention may also be advantageously carried out under pressure of an inert gas such as nitrogen. In said eventuality, a pressure ranging from 1.5 bar to 20 Kbar, preferably from 2 to 200 bar, may be used.

The invention will now be described in further details by way of the following examples, wherein the abbreviations have the usual meaning in the art, the temperatures are indicated in degrees centigrade (° C.); the NMR spectral data were recorded with a 360 MHz machine in CDCl$_3$, the chemical displacement δ are indicated in ppm with respect to the TMS as standard, the coupling constant J are expressed in Hz and all the abbreviations have the usual meaning in the art.

EXAMPLE 1

Preparation of Methyl 2-acetyl-3,3-dimethyl-5-oxohexanoate

A suspension of 0.135 g of Cu(acac)$_2$ (0.517 mmole) is stirred at 25° C. in 0.7 g of ethylacetate. Boron trifluoride etherate (0.154 g; 1.08 mmole) is added over 30 min. at 30° C. and agitation is continued for 2 h. The resulting homogeneous solution is added as such to a mixture of 6 g of methyl 3-oxo-butanoate (51.7 mmole) and 5.07 g of 4-methyl-3-penten-2-one (51.7 mmole). The resulting solution is stirred at room temperature over 16 h and finally heated at 60° C. for an hour. After cooling down to 30° C., 1.5 g of cyclohexane is added and the solution is stirred vigorously in the presence of 2.25 g of a 20% aqueous solution of Na$_4$EDTA. After the removal of the aqueous phase the resulting organic layer is washed with 2 g of 20% aqueous potassium carbonate and then with 2 g of a saturated sodium chloride solution.

The solvent and the unreacted material (starting materials) are distilled out under reduced pressure. The oily residue is distilled, in a bulb to bulb apparatus, at 110–130° C. under 1–2 mbar. 4 g of methyl 2-acetyl-3,3-dimethyl-5-oxo-hexanoate are obtained (>95% purity) corresponding to 36% yield.

$^1$H-NMR 1.16(s, 6H); 2.11(s, 3H); 2.21(s, 3H); 2.72(d.d, 2H); 3.71(s, 3H); 4.12(s, 1H).

$^{13}$C-NMR: 25.7(q); 26.1(q); 31.7(q); 31.9(q); 35.6(s); 51.9(q); 52.0(t); 63.7(d); 169.7(s); 203.4(s); 208.4(s).

MS: 214(M$^+$, 0.8); 172(6.0); 157(38.0); 139(10.0); 125 (77.8); 116(58.5); 115(92.0); 99(80.0); 83(99.2); 55(42.5); 43(100.0); 29(34.0).

EXAMPLE 2

Preparation of 3-acetyl-4,4-dimethyl-2,6-heptanedione

A suspension of 0.135 g of Cu(acac)$_2$ (0.517 mmole) is stirred at 25° C. in 0.7 g of ethylacetate. Boron trifluoride etherate (0.154 g; 1.08 mmole) is added over 30 min. at 30° C. and agitation is continued for 2 h. The resulting homogeneous solution is added as such to a mixture of 6 g of 2,4-pentanedione (60 mmole) and 5.88 g of 4-methyl-3-penten-2-one (60 mmole). The resulting solution is stirred at room temperature over 6 h and finally heated at 50° C. for an hour. After cooling down to 30° C., 1.5 g of cyclohexane is added and the solution is stirred vigorously in the presence of 2.25 g of a 20% aqueous solution of Na$_4$EDTA. After the removal of the aqueous phase the resulting organic layer is washed with 2 g of 20% aqueous potassium carbonate and then with 2 g of a saturated sodium chloride solution.

The solvent and the unreacted material (starting materials) are distilled out under reduced pressure. The oily residue is distilled, in a bulb to bulb apparatus, at 100–120° C. under 1–2 mbar. 3.8 g of 3-acetyl-4,4-dimethyl-2,6-heptanedione are obtained (90% purity) corresponding to 28% yield.

$^1$H-NMR: 1.16(s, 6H); 2.11(s, 3H); 2.21(s, 6H); 2.68(s, 2H); 4.37(s, 1H).

$^{13}$C-NMR: 26.3(q); 26.3(q); 31.9(q); 32.7(q); 32.7(q); 36.4(s); 52.2(t); 71.2(d); 204.9(s); 204.9(s); 208.6(s).

MS: 198(M$^+$, 0.1); 165(1.2); 156(4.3); 141(12.5); 123 (7.6); 99(59.9); 83(12.8); 55(4.5); 43(100.0); 29(3.4).

EXAMPLE 3

Preparation of Methyl 2-acetyl-3,4-dimethyl-5-oxohexanoate

A suspension of 0.135 g of Cu(acac)$_2$ (0.517 mmole) is stirred at 25° C. in 0.7 g of ethylacetate. Boron trifluoride etherate (0.154 g; 1.08 mmole) is added over 30 min. at 30° C. and agitation is continued for 2 h. The resulting homogeneous solution is added as such to a mixture of 6 g of methyl 3-oxo-butanoate (51.7 mmole) and 5.07 g of 3-methyl-3-penten-2-one (51.7 mmole). The resulting solution is stirred at room temperature. After cooling down to 30° C., 1.5 g of cyclohexane is added and the solution is stirred vigorously in the presence of 2.25 g of a 20% aqueous solution of Na$_4$EDTA. After the removal of the aqueous phase the resulting organic layer is washed with 2 g of 20% aqueous potassium carbonate and then with 2 g of a saturated sodium chloride solution.

The solvent and the unreacted material (starting materials) are distilled out under reduced pressure. The oily residue is distilled, in a bulb to bulb apparatus, at 110–130° C. under 1–2 mbar. 6.5 g of methyl 2-acetyl-3,4-dimethyl-5-oxo-hexanoate (mixture of 4 diastereoisomers) are obtained, corresponding to 58.5% yield.

$^1$H-NMR: 0.78, 0.83, 0.95–1.05, 1.12(d, 6H); 2.15, 2.18 (s, 3H); 2.21, 2.22, 2.23, 2.27(s, 3H); 2.60, 2.80(m, 2H); 3.50, 3.80(d, 1H); 3.68, 3.72, 3.74, 3.75(s, 3H).

$^{13}$C-NMR: 9.64, 10.91, 12.52, 12.63, 13.93, 14.36, 14.77, 15.09(q); 28.38, 28.68, 29.45, 29.49, 29.53, 29.66, 30.03, 30.37(q); 33.14, 33.47, 34.90, 35.71(d); 48.17, 48.50, 49.31, 49.47(d); 52.24, 52.38, 52.38, 52.55(q); 61.20, 61.95, 63.10, 63.53(d); 169.3(s); 202.3, 202.5, 202.9, 202.9(s); 210.6, 211.0, 211.3, 211.9(s).

MS: 214(M$^+$); 196; 183; 171; 167; 159; 143; 139; 129; 116; 111; 101; 99; 97; 85; 72; 69; 43.

What is claimed is:

1. A compound selected from the group consisting of methyl 2-acetyal-3,3-dimethyl-5-oxo-hexanoate, 3-acetyl-4,4-dimethyl-2,6-heptanedione and methyl 2-acetyl-3,4-dimethyl-5-oxo-hexanoate.

2. A process for the preparation of a compound of formula (III):

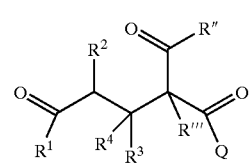

(III)

wherein

Q is selected from the group consisting of R' and OR' group;

R$^1$, R', and R" are selected, independently from each other, from the group consisting of a linear C$_1$–C$_5$ alkyl group, linear C$_1$–C$_5$ alkenyl group, a C$_1$–C$_4$ alkyl group, a C$_1$–C$_4$ alkenyl group, a C$_1$–C$_4$ alkoxy group, a C$_5$–C$_6$ cycloalkyl group, and a cycloalkenyl group;

R'" is selected from the group consisting of a hydrogen atom, and a linear or branched C$_1$–C$_3$ alkyl group; and R$^2$, R$^3$, and R$^4$ are selected, independently from each other, from the group consisting of a hydrogen atom, a linear $C_1$–$C_5$ alkyl group, a linear $C_1$–$C_5$ alkenyl group, a $C_1$–$C_4$ alkyl group, a $C_1$–$C_4$ alkenyl group, a $C_1$–$C_4$ alkoxy group, a $C_5$–$C_6$ cycloalkyl group, and a $C_5$–$C_6$ cycloalkenyl group;

wherein at least two of said $R^2$, $R^3$ and $R^4$ groups do not represent simultaneously an hydrogen atom;

which comprises reacting a β,β- or a α,β-disubstituted, or a α,β,β-trisubstituted, α,β-unsaturated ketone (I)

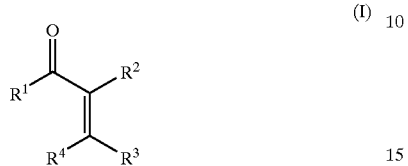

(I)

wherein $R^1$, $R^2$, $R^3$ and $R^4$ have the same meaning as in formula (III), with a β-ketoester or a β-diketone (II)

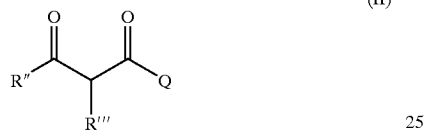

(II)

wherein Q, R″ and R‴ have the same meaning as in formula (III), in the presence of a catalyst of formula $M(X)_n$, wherein M is selected from the group consisting of a 3d transition metal, a lanthanide, a trimethylsilane group, a vanadyl group, an alkaline metal, Sc, Y, Sn, Pb, Al and Bi;

n is an integer from 1 to 3; and

X is selected from the group consisting of $CF_3SO_3^-$, $RSO_3^-$, $SbF_6^-$, $PF_6^-$, $ClO_4^-$, $[BF_3(RCOCRCOR)]^-$, $[BF_3(RCOCRCO_2R)]^-$, $[BF_3(RCOO)]^-$, $[BF_3(RO)]^-$, and $BF_4^-$, with R selected from the group consisting of an $C_1$–$C_{10}$ aromatic, alkylaromatic or alkyl group, halides atoms, and $C_1$–$C_6$ alkyl or alkoxy groups.

3. The process according to claim 2, wherein M is selected from the group consisting of Cu, Zn, Y and Yb, n represents an integer from 1 to 3 and X being selected from the group consisting of $CF_3SO_3^-$, $C_6H_5SO_3^-$, $CH_3C_6H_4SO_3^-$, $CH_3SO_3^-$, $SbF_6^-$, $PF_6^-$, $ClO_4^-$, $[BF_3(CH_3COCHCOCH_3)]^-$, $[BF_3(CH_3COO)]^-$, $BF_4^-$ and $BPh_4^-$.

4. The process according to claim 2, which further comprises preparing catalyst in situ by reacting an appropriate anhydrous metal salt of formula $M(CH_3COCHCOCH_3)_n$ or $M(R''''COO)_n$, wherein R'''' is selected from the group consisting of a $C_1$–$C_{10}$ aromatic, $C_1$–$C_{10}$ alkylaromatic, $C_1$–$C_{10}$ alkyl group, halide atoms, $C_1$–$C_6$ alkyl, $C_1$–$C_6$ alkoxy groups and non-coordinating nitrogen containing groups; n is an integer from 2 to 3, with n equivalents, with respect to the metal, of $BF_3\cdot OEt_2$ in a solvent.

5. The process according to claim 2, which further comprises preparing the catalyst in situ by dehydration of a hydrate form of the catalyst.

6. The process according to claim 2, which further comprises conducting the reaction in a solvent having with a water content of below 0.5% by weight, with the solvent selected from the group consisting of $C_4$–$C_6$ ethers, $C_2$–$C_8$ esters, $C_3$–$C_6$ ketones, acetic acid, methylene chloride and mixtures thereof.

7. The process according to claim 2, which further comprises conducting the reaction without a solvent.

8. The process according to claim 2, wherein $R^1$ $R'$ and $R''$ are independently selected from the group consisting of a linear $C_1$–$C_5$ alkyl and alkenyl group;

$R^2$, $R^3$ and $R^4$ are independently selected from the group consisting of a hydrogen atom, a linear $C_1$–$C_5$ alkyl and an alkenyl group, provided that at least two of said $R^2$, $R^3$ and $R^4$ groups do not represent simultaneously an hydrogen atom; and R represents a $C_1$–$C_{10}$ aromatic, alkylaromatic or alkyl group.

9. The process according to claim 8, which further comprises preparing the catalyst in situ by reacting an appropriate anhydrous metal salt of formula $M(CH_3COCHCOCH_3)_n$ or $M(R''''COO)_n$, R'''' being an $C_1$–$C_{10}$ aromatic, alkylaromatic or alkyl group, and n being an integer of 2 or 3, with n equivalents, with respect to the metal, of $BF_3\cdot OEt_2$ in a solvent.

10. The process according to claim 2, wherein the α,β-unsaturated ketone (I) is 4-methyl-3-penten-2-one or 3-methyl-3-penten-2-one and the β-ketoester (II) is a $C_1$–$C_4$ alkyl ester of the 3-oxo-butanoate or 2,4-pentanedione.

11. The process according to claim 10, wherein M is selected from the group consisting of Cu, Zn, Y and Yb, n represents an integer from 1 to 3 and X is selected from the group consisting of $CF_3SO_3^-$, $C_6H_5SO_3^-$, $CH_3C_6H_4SO_3^-$, $CH_3SO_3^-$, $SbF_6^-$, $PF_6^-$, $ClO_4^-$, $[BF_3(CH_3COCHCOCH_3)]^-$, $[BF_3(CH_3COO)]^-$, $BF_4^-$ and $BPh_4^-$.

12. The process according to claim 10, which further comprises preparing the catalyst in situ by reacting an appropriate anhydrous metal salt of formula $M(CH_3COCHCOCH_3)_n$ or $M(R''''COO)_n$, wherein R'''' is selected from the group consisting of a $C_1$–$C_{10}$ aromatic group, $C_1$–$C_{10}$ alkylaromatic group, a $C_1$–$C_{10}$ alkyl group, halide atoms, a $C_1$–$C_6$ alkyl group, a $C_1$–$C_6$ alkoxy group and non-coordinating nitrogen containing groups; and n is an integer of 2 or 3, with n equivalents, with respect to the metal, of $BF_3\cdot OEt_2$ in a solvent.

13. The process according to claim 10, which further comprises preparing the catalyst in situ by dehydration of a hydrate form of the catalyst.

14. The process according to claim 10, which further comprises conducting the reaction in a solvent having with a water content of below 0.5% by weight, with the solvent selected from the group consisting of $C_4$–$C_6$ ethers, $C_2$–$C_8$ esters, $C_3$–$C_6$ ketones, acetic acid, methylene chloride and mixtures thereof.

15. The process according to claim 10, which further comprises conducting the reaction without a solvent.

* * * * *

UNITED STATES PATENT AND TRADEMARK OFFICE
CERTIFICATE OF CORRECTION

PATENT NO. : 6,686,498 B2  Page 1 of 1
DATED : February 3, 2004
INVENTOR(S) : Jacoby It is certified that error appears in the above-identified patent and that said Letters Patent is hereby corrected as shown below:

Column 6,
Line 62, change "and a cycloalkenyl group;" to -- and a $C_5$-$C_6$ cycloalkenyl group; --.

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,686,498 B2
DATED : February 3, 2004
INVENTOR(S) : Jacoby

It is certified that error appears in the above-identified patent and that said Letters Patent is hereby corrected as shown below:

Title page,
Item [56], References Cited, OTHER PUBLICATIONS,
"Garcia-Raso et al." reference, change "Garcia-Raso,et al, to -- Garcia-Raso et al., --
"J.D. Surmatis et al." reference, delete "Technical Dept, Hoffman-La Roche," and insert -- The Journal of Organic Chemistry, --.
"Pavel Kočovsky et al." reference, (first occurrence), change "Koĉovsky" to -- Kočovsky -- and after "Transition-Metal", change "catalysts" to -- catalysis --;
"Pavel Kočovsky et al." reference, (second occurrence), change "Koĉovsky" to -- Kočovsky -- and after "Transition-Metal", change "catalysts" to -- catalysis --; before "Czechovoslak Chem." change "Collections" to -- Collection --; and after "pp. 2667–2674", change "(1986)" to -- (1988) --.
"William G. Dauben et al." reference, change "β-Distributed" to -- β-Disubstituted --; and after "pp. 3841-3844", change "(1993)" to -- (1983) --.
"Alfonso Fernandez-Mateos et al." reference, change "Alfonso Fernandez-Mateos" to -- Alfonso Fernandez-Mateos et al. --; and change "Acid, "Journal of Org, Chem.," to -- Acid," Journal of Org. Chem., --
"A.M. El-Gendy" reference, change "diethy" to -- diethyl --; change "8a-anthracenedicarboxykylate" to -- 8a-anthracenedicarboxylate --; and change "pp. 168-169" to -- pp. 168-179 --.
"Yuan Chow et al." reference, change "Yuan L. Chow etal.," to -- Yuan L. Chow et al., --;and change "Can. J. Chem 71, Vol 71," to -- Can J. Chem., Vol. 71, --.
"Abstract (XP-002195727)", delete "Royal Society of Chemistry,pp 157-162" and insert -- Green Chem., Vol. 1, No. 3, pp. 157-162 --.
"Soriente et al." reference, change "EU+3-Cataly6zed" to -- Eu$^{+3}$-Catalyzed --; and delete "Elsevier Science Ltd., --.
"H. Kotsuki et al", reference, change "Yb(Otf)$_3$-Catalyzed" to -- Yb(OTf)$_3$ --; and delete "Dept. of Chemistry,".

Signed and Sealed this

Seventeenth Day of August, 2004

JON W. DUDAS
*Acting Director of the United States Patent and Trademark Office*